(12) United States Patent
Pelc

(10) Patent No.: US 7,145,981 B2
(45) Date of Patent: *Dec. 5, 2006

(54) VOLUMETRIC COMPUTED TOMOGRAPHY (VCT)

(75) Inventor: Norbert J. Pelc, Los Altos, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/184,537

(22) Filed: Jul. 19, 2005

(65) Prior Publication Data
US 2006/0002506 A1 Jan. 5, 2006

Related U.S. Application Data

(63) Continuation-in-part of application No. 10/226,096, filed on Aug. 22, 2002.
(60) Provisional application No. 60/314,943, filed on Aug. 24, 2001.

(51) Int. Cl.
G21K 1/12 (2006.01)
(52) U.S. Cl. .............................. 378/9; 378/12
(58) Field of Classification Search ................ 378/122, 378/4, 9, 12
See application file for complete search history.

(56) References Cited

U.S. PATENT DOCUMENTS 6,324,258 B1 * 11/2001 Beekman .................... 378/145

* cited by examiner

Primary Examiner—Edward J. Glick
Assistant Examiner—Hoon Song
(74) Attorney, Agent, or Firm—Lumen Intellectual Property Services

(57) ABSTRACT

The present invention provides a volumetric computed tomography (VCT) system capable of producing data for reconstructing an entire three-dimensional (3D) image of a subject during a single rotation without suffering from cone beam artifacts. The VCT system comprises an array of source positions distributed along a line parallel to an axis of rotation, a plurality of collimators, and an array of x-ray detectors. In a preferred embodiment, a reversed imaging geometry is used. A 2D array of source positions provides x-rays emanating from each focal spot toward an array of detectors. The x-rays are restricted by a collimator array and measured by a detector array separately per each source position. The axial extent of the source array and the detector array are comparable to or larger than the axial extent of the portion of the object being imaged.

19 Claims, 5 Drawing Sheets

VOLUMETRIC COMPUTED TOMOGRAPHY (VCT)

CROSS-REFERENCE TO RELATED APPLICATIONS

This application is a continuation in part of U.S. patent application Ser. No. 10/226,096 filed on Aug. 22, 2002, which claims the benefit of U.S. Provisional Application No. 60/314,943, filed Aug. 24, 2001.

FIELD OF THE INVENTION

The present invention relates generally to computed tomography (CT) systems and, more particularly, to volumetric CT (VCT) systems.

BACKGROUND OF THE INVENTION

Conventional x-ray imaging is based on the absorption of x rays as they pass through different parts of a patient's body. Depending on the absorption in a particular tissue such as muscle or lung, a different intensity of x rays will pass through and exit the body. During conventional x-ray imaging, the exiting or transmitted x rays are recorded with a detection device, such as an x-ray film or other image receptor, and provide a two dimensional projection image of the tissue within the patient's body. While these images can be very useful, when there is one structure in front or behind another, their images are superimposed in a single projection image and it is impossible to know which is in front, and each may obstruct the visibility of the other.

While also based on the variable absorption of x rays, Computed Tomography (CT) imaging provides a different form of imaging known as cross-sectional imaging. CT imaging, also known as Computerized Axial Tomography (CAT) scanning, has been developed and used for many years to generate images of cross-sectional planes or slices of anatomy. Each image is generated by a computer synthesis of x-ray transmission data obtained in many different directions in a given plane. Because CT scans reveal organs, bone, blood vessels, and soft tissues, including lung, muscles, and tumors, with great clarity and detail, CT systems are particularly useful as a diagnostic or therapeutic guidance tool for medical purposes. CT systems have also been known to be useful in industrial, security, and other systems where imaging data are to be obtained.

A CT system typically has a circular opening and includes an x-ray source and a detector array. A motorized table is commonly used to move a subject to be examined, such as an object, a patient, or a region of interest thereof, up or down and in or out of the circular opening. The x-ray source and the detector array are mounted on opposite sides of a rotating gantry. As the patient passes through the system, the x-ray source rotates around the inside of the circular opening. The x-ray source produces x-rays that pass through the patient and impinge on the detector array, which may be arc-shaped and also revolving. This process is also known as scanning.

In known third generation CT systems, the x-ray source, comprising an x-ray tube, provides x-rays emanating from a point commonly referred to as a "focal spot". The x-ray beam emanating from the focal spot to the array of detectors resembles the shape of a fan and therefore is sometimes referred to as a "fan beam". The narrow, fan-shaped beam of x rays is used to irradiate a section or slice of the patient's body. The thickness of the "fan beam" may be as small as 0.5 millimeter or as large as 10–20 millimeters. A typical scanning process usually involves many rotations, each generating a different slice. Thus, the scanning process could involve dozens or hundreds of rotations of the x-ray source around the patient in coordination with the motorized table through the circular opening.

The x-ray source is coupled to the detector array in a manner that the focal spot of the x-ray tube and the detector array are on one plane. The x-ray source and the detector array rotate together about an axis of rotation, such as an axis through the patient, perpendicular to the plane. For each position of the rotating gantry, the detector array records x rays exiting the section of the patient's body being irradiated as a projection, also known as a view or an x-ray profile. Many different views are collected during one complete rotation, typically a 360 degrees rotation. A single rotation takes about 1 second. During each rotation, the detectors may record about 1,000 views (x-ray profiles). The x-ray projection data collected/measured/sampled are then sent to a computer for reconstructing all of the individual views into a cross-sectional image (slice) of the internal organs and tissues for each complete rotation. Multiple computers are typically used to control the entire CT system. Despite the discrete nature of the sampled data, a number of known reconstruction algorithms are able to convert the collected data into high quality images of the slice. In this scanning mode, a three dimensional image can be made by producing images of slices, one at a time. The thickness of the slice and the spacing between slices are adjustable.

Most modern CT imaging systems are capable of performing "spiral", also called "helical", scanning as well as scanning in the more conventional "axial" mode as described above. Spiral CT systems are well known in the art. An exemplary teaching can be found in U.S. Pat. No. 5,966,422, "MULTIPLE SOURCE CT SCANNER," issued on Oct. 12, 1999 to Dafni et al. and assigned to Picker Medical Systems, Ltd. of Haifa, Israel.

Briefly, the term "spiral" comes from the shape of the path, relative to the object, taken by the x-ray beam during scanning. The motorized (examination) table advances at a constant rate through the scanning gantry while the x-ray source rotates continuously around the patient, tracing a spiral path relative to the patient. This spiral path gathers continuous x-ray profile data without gaps. The pitch of a spiral scan, or helix, is defined as how far the patient is translated during one rotation divided by the thickness of the fan beam. In a typical procedure, the pitch ranges from about 1 to 2. A single rotation takes approximately 0.5 to 1 second.

Some CT imaging systems, also called multi-detector CT or multi-row CT systems, are capable of imaging multiple slices simultaneously, allowing relatively larger volumes of anatomy to be imaged in relatively less time. In such a system, a number of planes or slices are sampled simultaneously via multiple rows of detectors. Since data for several slices can be obtained in one scan, total scanning time is greatly reduced. Exemplary teachings can be found in U.S. Pat. No. 6,047,040, "DETECTOR SIGNAL INTEGRATION IN VOLUMETRIC CT SCANNER DETECTOR ARRAYS," issued to Hu et al. on Apr. 4, 2000; and U.S. Pat. No. 6,137,857, "SCALABLE DETECTOR FOR COMPUTED TOMOGRAPH SYSTEM," issued to Hoffman et al. on Oct. 24, 2000 and assigned to General Electric Company of Milwaukee, Wis., USA.

However, these multi-detector or multi-row CT systems still require more than one revolution during image scanning to produce data for a thick volume. A logical extension to the multi-slice or multi-detector scanning mode is called a cone beam CT. The goal is to enable the reconstruction of an entire three-dimensional (3D) object using a single rotation. Unfortunately, this imaging geometry suffers from several known drawbacks such as image artifacts, sometimes referred to as cone beam artifacts, and image reconstruction errors. Briefly, the divergence of the x-ray beam in the direction of the axis of rotation causes the reconstruction problem to be ill-posed. Indeed, even in multi-row CT systems, as the angle spanned by the multiple rows increases, so do the image reconstruction problems caused by the image artifacts. As such, the system will increasingly suffer from cone beam artifacts. Additionally, if one tries to reduce these artifacts by using more accurate reconstruction algorithms, image reconstruction can be computationally intensive and slow in cone beam CT systems.

SUMMARY OF THE INVENTION

Accordingly, it is a primary object of the present invention to provide a fast and reliable volumetric CT system capable of providing image data for reconstructing an entire 3D object using a single rotation without suffering from image artifacts such as cone beam artifacts, overcoming image reconstruction errors and beam divergence problems common in known cone-beam CT systems.

The goal is achieved in a CT system capable of providing data for reconstructing an entire 3D object using a single rotation, the system comprising, in a preferred embodiment, an array of x-ray sources distributed along a line parallel to an axis of rotation, a plurality of flat collimator plates positioned perpendicular to the axis of rotation and near the x-ray sources so to limit the x-rays illuminating the object to contain only x-rays that travel substantially along lines perpendicular to the axis of rotation, and a flat panel x-ray detecting means comprising an array of small and fast x-ray detectors for detecting and measuring transmitted x-rays emitted by the entire source array. In a preferred embodiment, a reversed imaging geometry is used. The x-ray source includes a 2D array of source positions and the detector is an array that spans the extent of the object being imaged in the direction parallel to the axis of rotation. Preferably a collimating means restricts the x-rays primarily to those directed at the detectors. The collimating means may be an array of collimators, one in front of each source position, or a piece of dense metal having a plurality of holes one in front of each source position.

Still further objects and advantages of the present invention will become apparent to one of ordinary skill in the art upon reading and understanding the following drawings and detailed description of the preferred embodiments. As it will be appreciated by one of ordinary skill in the art, the present invention may take various forms and may comprise various components and steps and arrangements thereof. As such, the drawings are for purposes of illustrating a preferred embodiment(s) of the present invention and thus are not to be construed as limiting the present invention.

DETAILED DESCRIPTION

Figure 1:
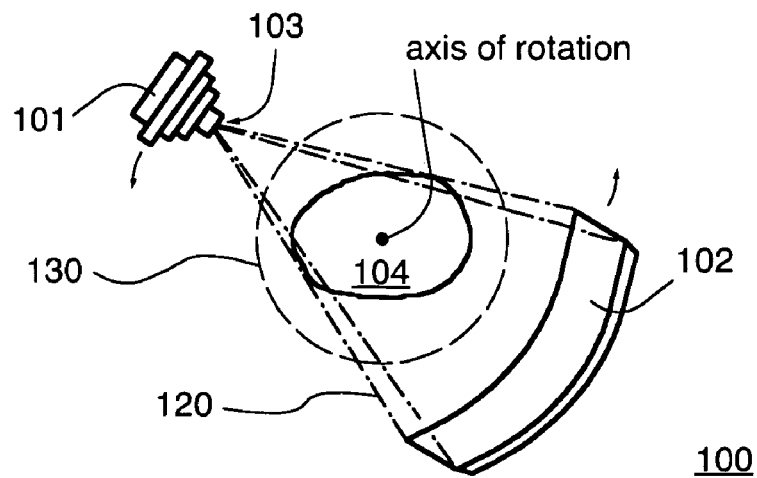
FIG. 1 illustrates the general principles of a cone beam CT system.

FIG. 1 illustrates a prior art cone beam CT system 100. System 100 includes an x-ray source 101, which employs an x-ray tube, for providing x-rays 120 emanating from a point 103, hereinafter referred to as the focal spot 103. The detector array 102 can be a wide arc or a flat 2-dimensional array containing dozens or hundreds of rows of x-ray detectors. Detector 102 measures x-rays emanating in all directions from the focal spot 103. The cone beam CT system 100 is characterized by the shape of x rays 120 emanated from the focal spot 103 onto the detector array 102. Both the x-ray source 101 and the detector array 102 may be mounted on a gantry (not shown), and may revolve around an axis of rotation of a circular opening 130. The gantry could be a C-arm. An object 104, typically a patient, is positioned in the circular opening 130 via an examination platform, e.g., a motorized table (not shown) that can move up or down and slide in or out of the circular opening 130, so as to place the region to be imaged within the x-ray beam.

As discussed herein, employing the many rows of detectors in array 102, system 100 can produce multiple slices at a time, thereby providing a relatively faster scanning of subject 104 than a conventional CT system with a fan-shaped beam in spiral (helical) scanning mode. However, as is well known in the art, this cone beam imaging geometry suffers from several drawbacks, such as image artifacts and image reconstruction errors, caused by the divergence of the x-ray beam in the direction of the axis of rotation. The divergence problem and hence the cone beam artifacts worsens as the number of rows in the detector array 102 increases. That is, in a multi-row or cone-beam CT system, as the angle spanned by the multiple rows increases, so do the image reconstruction problems caused by the cone beam artifacts.

The cone beam artifacts would be mitigated if, for each point in the object being imaged, x-ray transmission was measured along rays lying on the plane through the point and perpendicular to the axis of rotation, and in many directions through the point.

Figure 2:
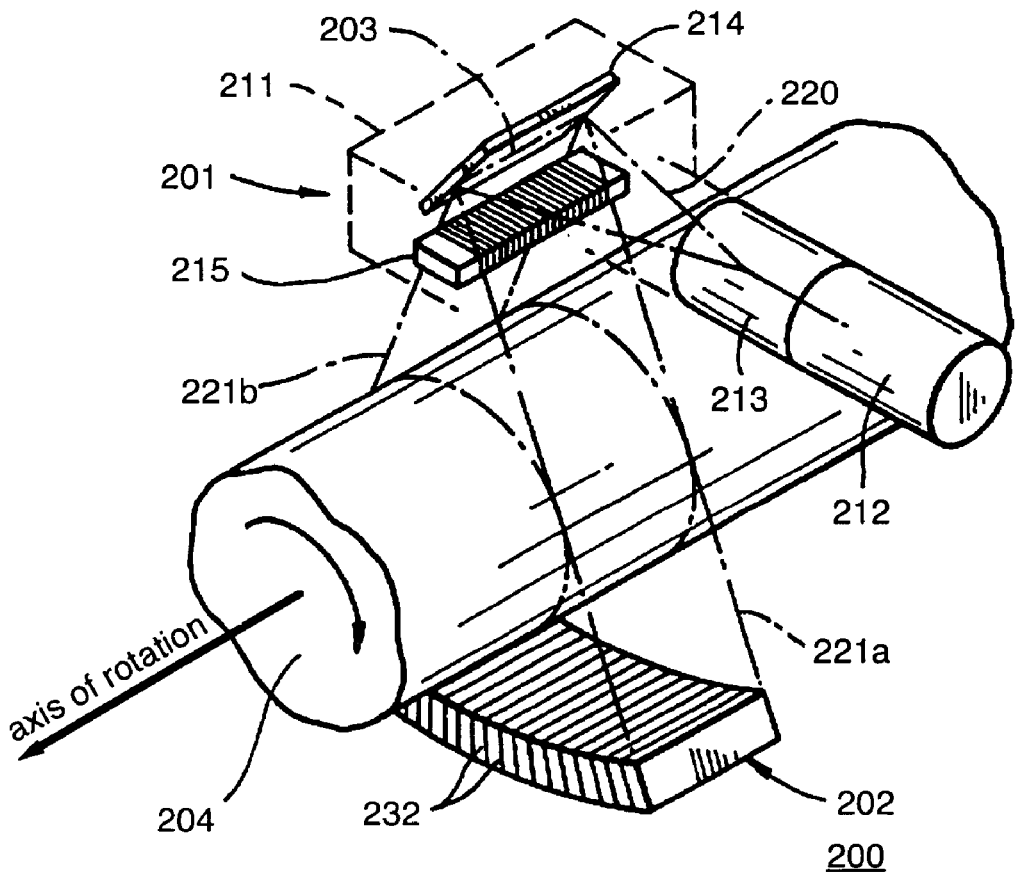
FIG. 2 is a representation of a prior art CT system.

FIG. 2 shows a prior art volumetric CT scanner 200. In system 200, a part of a human body 204 to be scanned is placed between an x-ray source 201 and an arc-shaped detector assembly 202. The x-ray source 201 is disposed in an evacuated envelope 211 including an electron gun assembly 212, a magnetic deflector assembly 213, a target 214, and a window (not shown) for passing x-rays to a vane collimator 215. The electron gun assembly 212 generates an electron beam 220, which is deflected by the magnetic deflector assembly 213. The target 214 receives the deflected electron beam 220 and generates cones of x rays responsive to the incident electron beam. The beam is linearly scanned across target 214 along a line 203 thereby generating a plurality of successive cone beams. The vane collimator 215 which includes a plurality of spaced parallel vanes forming a plurality of slots is placed opposite the target 214 and serves to pass only a thin fan beam of x-rays emanating from the point where the electron beam strikes the target. As the beam scans across the target successive adjacent fan beams are formed. The plurality of spaced adjacent fan beams traverse the volume of the object under examination as shown between the fan beams 221a and 221b. The detector 202 comprising a linear array of elongated detector elements 232 receives the x rays after they traverse the object 204.

In order to provide a CT image of the volume being scanned, the x-ray source 201 is rotated relative to the object 204 such that the plurality of scanned fan beams are transmitted over an angle of 180° plus the fan beam angle with respect to the object 204, although typically a 360° rotation is used. The output from each of the detector elements 232 can be amplified with a conventional preamplifier (not shown). The output is multiplexed and digitized by a conventional multiplexer and a conventional A/D converter (not shown). Sufficient data for reconstruction are obtained in this way. The digitized signals are stored in a cache (not shown) during acquisition. The stored digitized signals are conventionally processed in a reconstruction system (not shown) and applied to a display (not shown) for displaying a 3D image of the interior of the object 204. For further detailed teachings of system 200, readers are referred to U.S. Pat. No. 5,712,889, titled "SCANNED VOLUME CT SCANNER" and issued to Lanzara et al. on Jan. 27, 1998. In system 200, in order to acquire data for multiple slices, e.g., 40 slices, the detector signal must be sampled an equal amount, i.e., 40 times, for each angular position of the gantry. With an effective sampling speed of approximately 20 microseconds per detector, rendering a data rate of 50 thousand samples per second per detector, 50 million samples per second are collected for a system of 1,000 detectors.

Because the x-ray source position in the system of FIG. 2 is moved in the direction of the axis of rotation over a distance equal to the thickness of the volume being imaged, this system can be immune from cone beam artifacts. One limitation of the prior art system of FIG. 2 is that the resolution of the system in the direction of the axis of rotation is determined by the thickness of the fan beams emanating from the vane collimator 215. To obtain high resolution, the fan beams must be very thin, which can be difficult to achieve. In addition, restricting the x-rays to such thin fan beams discards the vast majority of the x-rays generated in source 201, which could lead to a high image noise level, or a long scan time to allow a sufficient number of x-rays to be detected.

Figure 3:
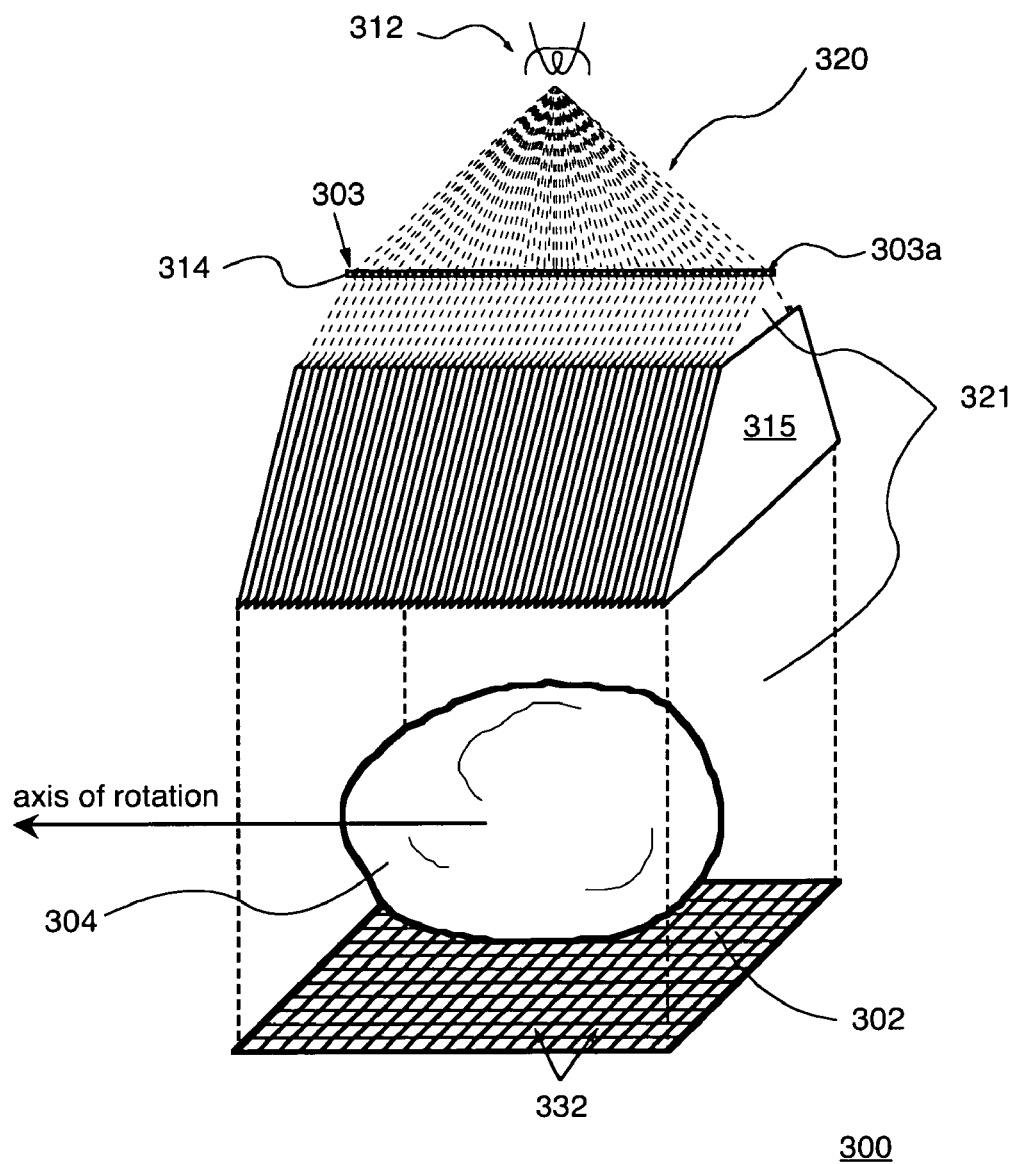
FIG. 3 is a representation of a VCT system according to a first embodiment of the present invention.

Referring to FIG. 3, an improved VCT system 300 according to a first embodiment of the present invention is illustrated. System 300 is capable of producing data to reconstruct a large number of slices in a single rotation in a fast and reliable manner without suffering from cone beam artifacts. Like the system of FIG. 2, system 300 comprises an x-ray source with an array of source positions 303, including source position 303a, distributed along a line parallel to the axis of rotation, and with an axial extent comparable to the extent of an subject 304 to be imaged in this direction, as shown in FIG. 3. The source could function, like the sources in system 200 of FIG. 2, by scanning an electron beam 320 along a line on the target 314. The linear anode 314 may be a copper block with a target made of another metal plated on or embedded in the copper surface. The metal is most often tungsten, but other metals can be used, such as molybdenum, or rhodium.

During operation, electrons are produced at the cathode 312 and accelerated to the target 314. Interactions between high energy electrons of the electron beam 320 and atoms of the target 314 cause deceleration of the electrons and production of x-ray photons 321. The accelerating potential (e.g., 150 kV) determines the spectrum of wavelengths (or photon energies) of the emitted x-rays 321. The cathode 312 and the target 314 (and hence the source positions 303) are positioned in an evacuated housing (not shown). The electron beam 320 can be steered by electromagnetic steering means, such as electromagnetic coils (not shown), positioned inside or outside of the housing. X-rays 321 emanate in all directions from each focal spot (source) positions 303 and exit the housing through an x-ray transparent window of the housing (not shown). This x-ray source is substantially similar to the electron gun assembly 212, steering means, target 214, and window of system 200 of FIG. 2.

According to an aspect of the invention, in contrast to the prior art system of FIG. 2, an array 302 of x-ray detectors elements 332 is used to measure the transmitted x-rays 321 that were emitted from each point in the source array 303. The detector array 302 is a two dimensional array, i.e., multiple columns and rows, of small and fast x-ray detectors elements 332 arranged in a flat- or arc-shaped panel. Detector elements 322 are small and provide high resolution in both directions along the array, and in particular, provide resolution in the axial direction, i.e., the direction of the axis of rotation of the system.

Figure 5:
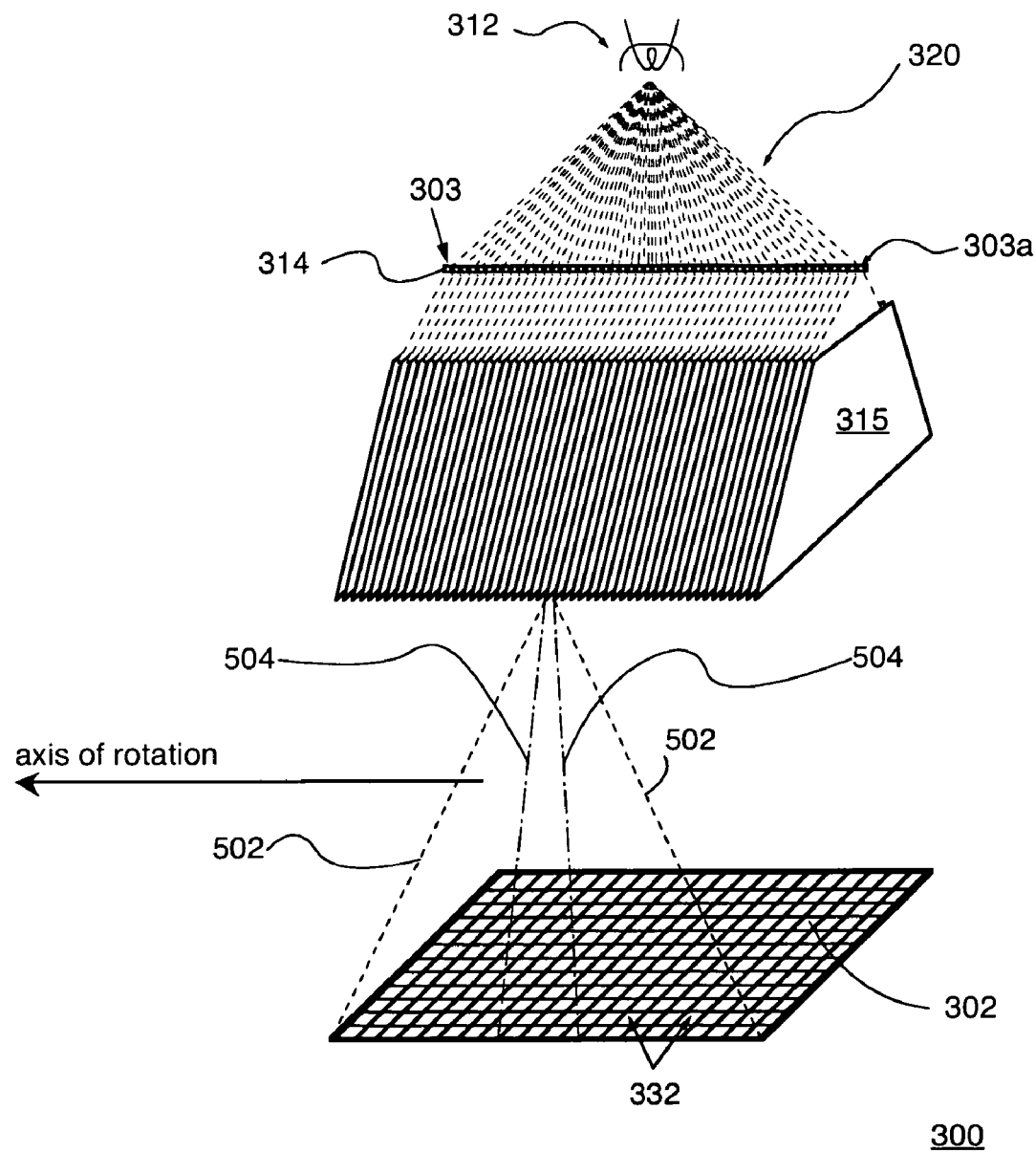
FIG. 5 shows X-ray illumination of part or all of an X-ray detector array according to an embodiment of the invention.

Thus, it is no longer necessary for the x-rays illuminating object 304 to be thin fan beams. An array of collimator vanes 315 can be used to somewhat limit the divergence of the x-rays in the direction of the axis of rotation, but this limitation need not be perfect. Thus, more of the x-rays produced by the source are allowed to illuminate the object, are detected, and are used to produce the volumetric CT image. Each source position illuminates more than one detector row. It may but need not illuminate the entire detector array. Such X-ray illumination of more than one but not all detector array rows by a source position is shown by lines 504 on FIG. 5. Such X-ray illumination of all detector array rows by a source position is shown by lines 502 on FIG. 5.

The x-ray source and the detector array 302 rotate about the axis of rotation. X-ray measurements through the object 304 are made as this structure rotates one revolution. These measurements provide line integrals of the distribution of attenuation coefficients for all lines through the subject 304 that are paths through which x-ray transmission measurements were made, i.e. lines connecting the source positions to the position of detector illuminated by that source position. Since the target point from which x-rays emanated at any point in time is controlled by the operation of the x-ray source and is therefore known, the line through which unscattered photons traveled is known precisely and is not ambiguous. Subject 304 is not limited to a patient or a region of interest thereof and can be any object from which imaging data are to be obtained, e.g., anatomy of a physical structure, such as internal structure of an animal, plant, or other organism, or of any of its parts.

Note that in this system there is some divergence of the x-ray beam in the axial direction, all x-rays do not travel along a set of planes that are parallel to each other and perpendicular to the axis of rotation (i.e., transaxial planes). However, the measured data are a superset of all projections needed for an accurate 3D image reconstruction. That is, given a sufficient number of sources, detectors, and views, the measured data will contain projection measurements for lines that lie on transaxial planes (in-plane rays) and also additional line integrals along lines that cross through planes (cross-plane rays). The in-plane rays are sufficient by themselves to provide an artifact-free image of all planes. The cross-plane rays can also be efficiently used to improve the signal-to-noise ratio (SNR) of the image without introducing cone beam artifacts. When the divergence is small, algorithms similar to those used in conventional multi-detector CT systems or variations of the so-called "Feldkamp" method could be used. When the divergence is larger or when accurate reconstructions are necessary, algorithms that properly use all the data should be used. Reconstruction algorithms that are able to do this are well known in the art, e.g., in Pelc, N. J., "A Generalized Filtered Backprojection Algorithm for Three Dimensional Reconstruction", Doctoral dissertation, Harvard University, 1979. Such algorithms are also used in 3D PET, and thus are not further described herein.

The x-ray detector elements employed are preferably very fast since they must measure separate x-ray readings for each source position and each view. The faster the detector elements, the faster data can be collected for the entire volume in one revolution. To be able to image a large object with high spatial resolution, detector array 302 must be large and contain a large number of detector elements. This need for a large number of very fast detectors is avoided in the system of FIG. 4.

Figure 4:
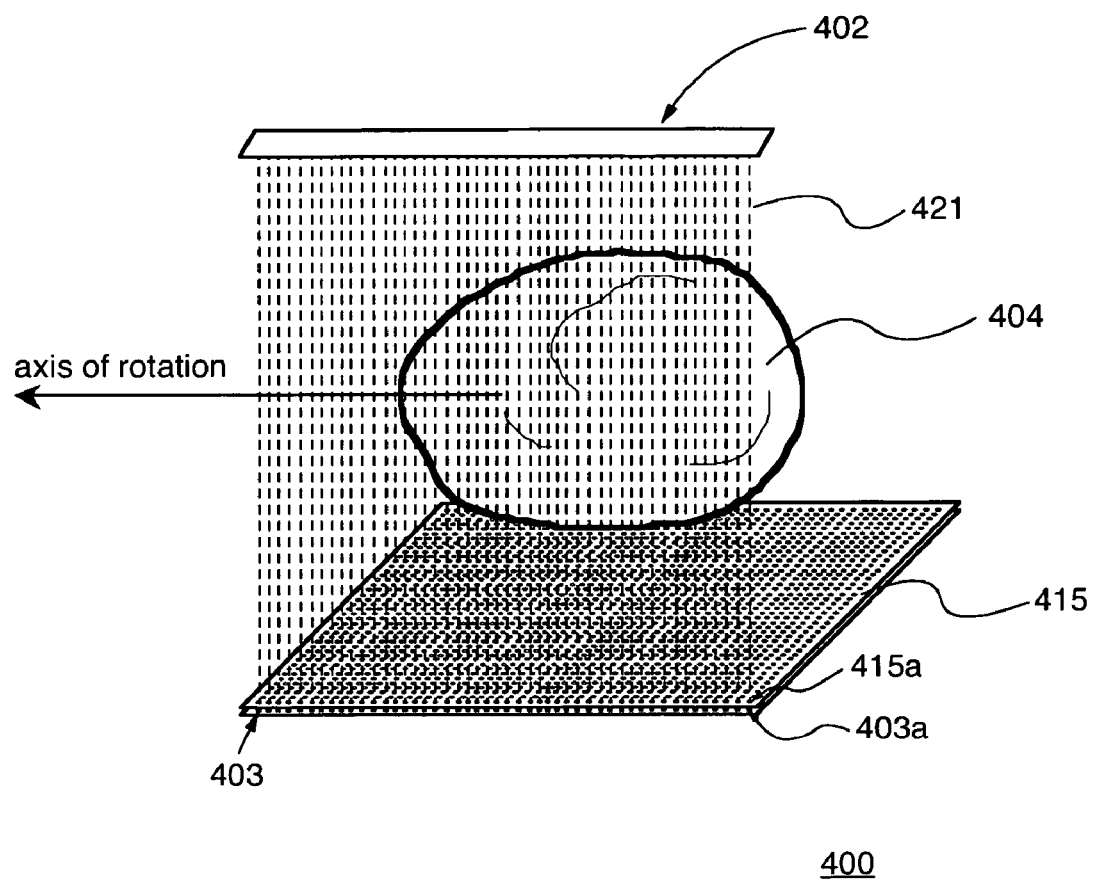
FIG. 4 is a representation of a VCT system according to a second embodiment of the present invention.

A preferred embodiment of the present invention will now be described with reference to FIG. 4, where a reversed imaging geometry compared to FIG. 3 is illustrated. In FIG. 4, a VCT system 400 comprises a 2D array, e.g., 100×100, of source positions 403, including source position 403a, and a detector array 402. Both the source array and the detector array are as long in the axial direction as the region being imaged. While the detector array 402 in this system is as long in the axial direction as detector 302 of the system shown in FIG. 3, it need not be as wide, and therefore can contain fewer detector elements. An electron beam (not shown) is produced and accelerated, and is steered to land on the source positions 403 by steering means (not shown) An array 415 of collimators, one in front of each source position, restricts x-rays to those x-rays 421 directed at the detector array 402. The collimator array 415 comprises a plurality of holes, one corresponding to each of source positions 403. For example, as shown in FIG. 4, hole 415a corresponds to source position 403a. While in FIG. 4 x-rays appear to all be traveling on paths that are parallel to the axis of rotation, this need not be so. During a single revolution, an electron beam scans the x-ray source array 403, one source position at a time, many, many times (e.g., hundreds or thousands). Each element of the detector array 402 acquires x-ray measurements for each source position, and since the point from which x-rays were generated at any point in time is known, the projection line corresponding to each measurement is also known. The x-ray measurements are used for image reconstruction of the subject 404 in the same manner and with the same algorithm as in the system of FIG. 3, e.g., processing the measured data in a computer (not shown) equipped with appropriate image reconstruction algorithms and software. The detector array 402 can be but need not be a single line (column) of detector elements. Components needed for this system such as a 2D scanned anode x-ray source and arrays of small and fast detector elements have been developed by NexRay Inc., Los Gatos, Calif., U.S.A.

Figure 6:
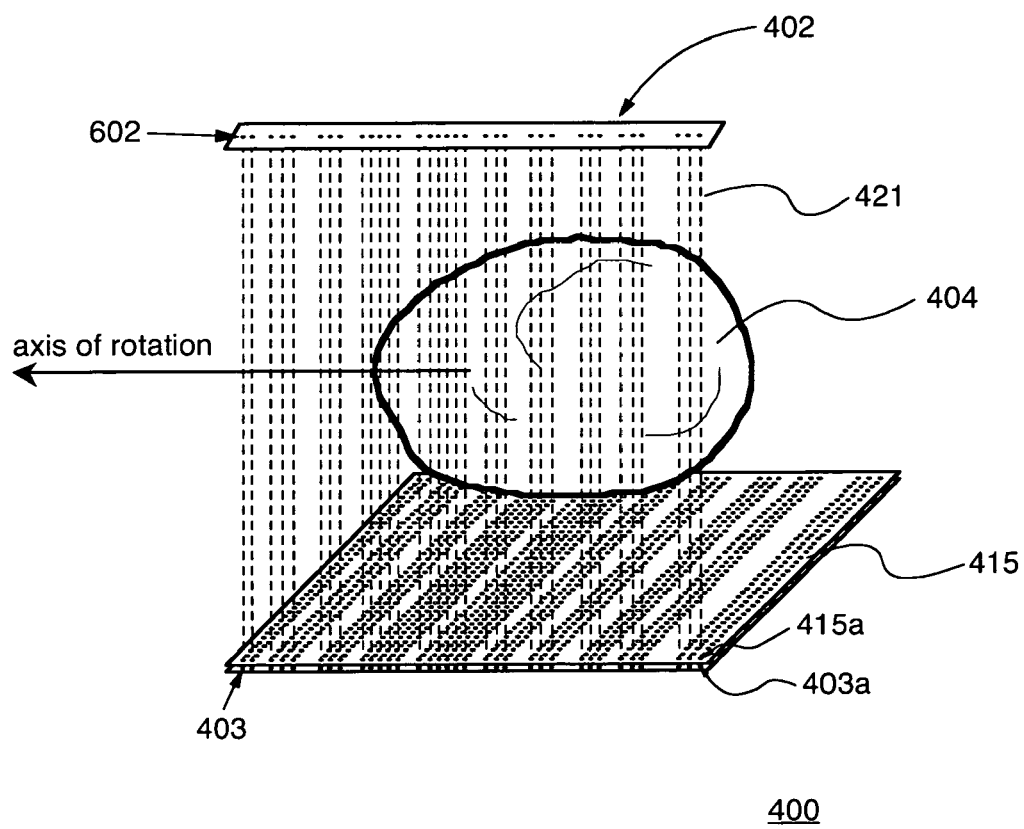
FIG. 6 shows unequal source and detector spacings for the embodiment of FIG. 4.

FIG. 6 shows unequal source and detector spacings for the embodiment of FIG. 4. In this embodiment, source array 403 has unequal spacing along the axis or rotation, and detector array elements 602 are also unequally spaced along the axis of rotation.

Although the present invention and its advantages have been described in detail, it should be understood that various changes, substitutions, and alternations can be made without departing from the principles and the scope of the present invention. For example, the source and/or detector arrays can have equally spaced elements. Alternatively, the source and/or detector arrays can have unequally spaced elements. Such equal or unequal element spacing can be in either (or both) of the directions of a two-dimensional source or detector array. Some embodiments of the invention include a collimator as described above, and other embodiments do not include such a collimator. The source array can use a single scanned electron beam, as described above, or as an alternative multiple cathodes can be used (in the limit, one cathode for each source position) as long as the source position from which the x-rays illuminating each detector element is known or can be determined. Accordingly, the scope of the present invention should be determined by the following claims and their legal equivalents.

What is claimed is:

1. A volumetric computed tomography (VCT) system for producing, in one single rotation, x-ray measurements for reconstructing a plurality of image slices through a portion of a subject positioned along an axis of rotation, the VCT system comprising:
   an x-ray source array having a plurality of source positions for producing x-rays emanating from each of the source positions, wherein the x-ray source positions are arranged in a two-dimensional array having an extent in the direction of the axis of rotation;
   an x-ray detector array for acquiring x-ray measurements for each of the source positions separately, the x-ray detector array including x-ray detector elements that are spaced one from the other in the direction of the axis of rotation; and
   means for rotating the source array and the detector array about the axis of rotation,
   wherein the x-ray source array and the x-ray detector array have comparable extent along the direction of the axis of rotation.

2. The VCT system of claim 1, further comprising a collimator to partly limit the divergence of the x-rays emanating from each of the source positions, wherein the divergence is partly limited in the direction of the axis of rotation, and wherein each source position illuminates multiple x-ray detector elements in the direction of the axis of rotation.

3. The VCT system of claim 2 wherein each source position illuminates a substantial fraction of the x-ray detector elements in the direction of the axis of rotation.

4. The VCT system of claim 3 wherein each source position illuminates the entire array of detector elements in the direction of the axis of rotation.

5. The VCT system of claim 1, wherein said x-ray source positions are equally spaced in at least one direction.

6. The VCT system of claim 1, wherein said x-ray source positions are unequally spaced in at least one direction.

7. The VCT system of claim 1, wherein detector elements in said detector array are equally spaced in at least one direction.

8. The VCT system of claim 1, wherein detector elements in said detector array are unequally spaced in at least one direction.

9. The VCT system of claim 1, wherein said x-ray source array is a two-dimensional scanned anode x-ray source.

10. The VCT system of claim 1 wherein the array of detector elements is a two-dimensional array.

11. The VCT system of claim 1 wherein the array of detector elements is a one-dimensional array.

12. A method of volumetric computed tomography comprising:

producing x-rays from a plurality of source positions arranged in a two-dimensional array having an extent in the direction of an axis of rotation;

passing the x-rays from each source position through an object to produce transmitted x-rays from each source position;

measuring the transmitted x-rays from each source position with a detector array, the detector array containing elements separated in the direction of the axis of rotation; and rotating the source and the detector array around the axis of rotation;

wherein the plurality of source positions and the detector array have comparable extent in the direction of the axis of rotation.

13. The method of claim 12, further comprising partly limiting a divergence of the x-rays from each source position using a collimator, wherein the divergence is partly limited in the direction of the axis of rotation such that the x-rays exiting the collimator do not all travel in a plane substantially perpendicular to the axis of rotation, and wherein each source position illuminates multiple elements separated in the direction of the axis of rotation.

14. The method of claim 12 wherein each source position illuminates a substantial fraction of the x-ray detector elements in the direction of the axis of rotation.

15. The method of claim 13 wherein each source position illuminates the entire array of detector elements in the direction of the axis of rotation.

16. The method of claim 12 wherein said detector array forms a one-dimensional linear array.

17. The method of claim 12 wherein said detector array forms a two-dimensional array.

18. The method of claim 12 wherein said plurality of source positions have an axial extent comparable or exceeding the axial extent of the object.

19. The method of claim 12 wherein said detector array has an axial extent comparable or exceeding the axial extent of the object.

* * * * *